(12) United States Patent
Lob

(10) Patent No.: US 6,833,007 B2
(45) Date of Patent: *Dec. 21, 2004

(54) ENDOPROTHESIS

(76) Inventor: Guenter Lob, Ehrwalder Str. 82, D-81377 Munich (DE)

(*) Notice: Subject to any disclaimer, the term of this patent is extended or adjusted under 35 U.S.C. 154(b) by 39 days.

This patent is subject to a terminal disclaimer.

(21) Appl. No.: 10/167,583

(22) Filed: Jun. 13, 2002

(65) Prior Publication Data

US 2003/0033019 A1 Feb. 13, 2003

Related U.S. Application Data

(63) Continuation of application No. 09/242,410, filed as application No. PCT/DE97/01819 on Aug. 18, 1997, now Pat. No. 6,454,810.

(30) Foreign Application Priority Data

Aug. 16, 1996 (DE) .......................... 196 33 865

(51) Int. Cl.[7] ................................................. A61F 2/36
(52) U.S. Cl. ............................... 623/23.47; 623/16.11; 606/60; 606/64
(58) Field of Search ............................... 606/60, 61, 62, 606/63, 64, 65, 67, 72; 623/16.11, 17.11, 17.15, 17.16, 23.47

(56) References Cited

U.S. PATENT DOCUMENTS

| 3,670,724 A | 6/1972 | Bosacco |
| 3,709,218 A | 1/1973 | Halloran |
| 3,889,299 A | 6/1975 | Osborne et al. |
| 3,893,196 A | 7/1975 | Hochman |
| 3,900,025 A | 8/1975 | Barnes |
| 4,554,914 A | 11/1985 | Kapp et al. |
| 4,657,550 A | 4/1987 | Daher |
| 4,728,335 A | 3/1988 | Jurgutis |
| 4,787,907 A | 11/1988 | Carignan |
| 4,820,305 A | 4/1989 | Harms |
| 4,932,973 A | 6/1990 | Gendler |
| 4,938,768 A | 7/1990 | Wu |
| 5,281,226 A | 1/1994 | Davydov et al. |

(List continued on next page.)

FOREIGN PATENT DOCUMENTS

| DE | 20 49 111 | 4/1971 |
| DE | 33 24 103 | 11/1984 |
| DE | 33 47 055 | 7/1985 |
| DE | 35 28 728 | 2/1987 |
| DE | 41 29 724 | 3/1993 |
| EP | 0 281 984 | 9/1988 |

(List continued on next page.)

Primary Examiner—Corrine McDermott
Assistant Examiner—William H Matthews
(74) Attorney, Agent, or Firm—Venable LLP; Robert Kinberg

(57) ABSTRACT

An endoprosthesis for replacing osseous areas in the diaphysial and metaphysial region of a bone and for connecting separate segments of the bone includes at least one intramedullary securing member and an intermediate member having at least one end region and being divided longitudinally into two detachably connected part elements. Each at least one end region defines a respective recess so that when the two part elements are connected together, each at least one end region forms an axially extending passage that retains one of the at least one intramedullary securing members.

11 Claims, 7 Drawing Sheets

| U.S. PATENT DOCUMENTS | | | | FOREIGN PATENT DOCUMENTS | | |
|---|---|---|---|---|---|---|
| 5,334,184 A | | 8/1994 | Bimman | EP | 0 392 076 | 10/1990 |
| 5,336,223 A | | 8/1994 | Rogers | EP | 0 551 611 | 7/1993 |
| 5,352,227 A | | 10/1994 | O'Hara | EP | 642 775 | 3/1995 |
| 5,618,286 A | | 4/1997 | Brinker | EP | 0 649 639 | 4/1995 |
| 5,626,580 A | | 5/1997 | Brosnahan | EP | 0 729 732 | 9/1996 |
| 5,665,089 A | | 9/1997 | Dall | SU | 0 718 097 | 2/1980 |
| 5,871,484 A | * | 2/1999 | Spievack et al. ............. 606/60 | SU | 0 862 937 | 9/1981 |
| 5,980,522 A | | 11/1999 | Koros | WO | WO 94/18897 | 9/1994 |
| 6,019,761 A | | 2/2000 | Gustilo | | | |
| 6,454,810 B1 | * | 9/2002 | Lob ........................ 623/23.47 | * cited by examiner | | |

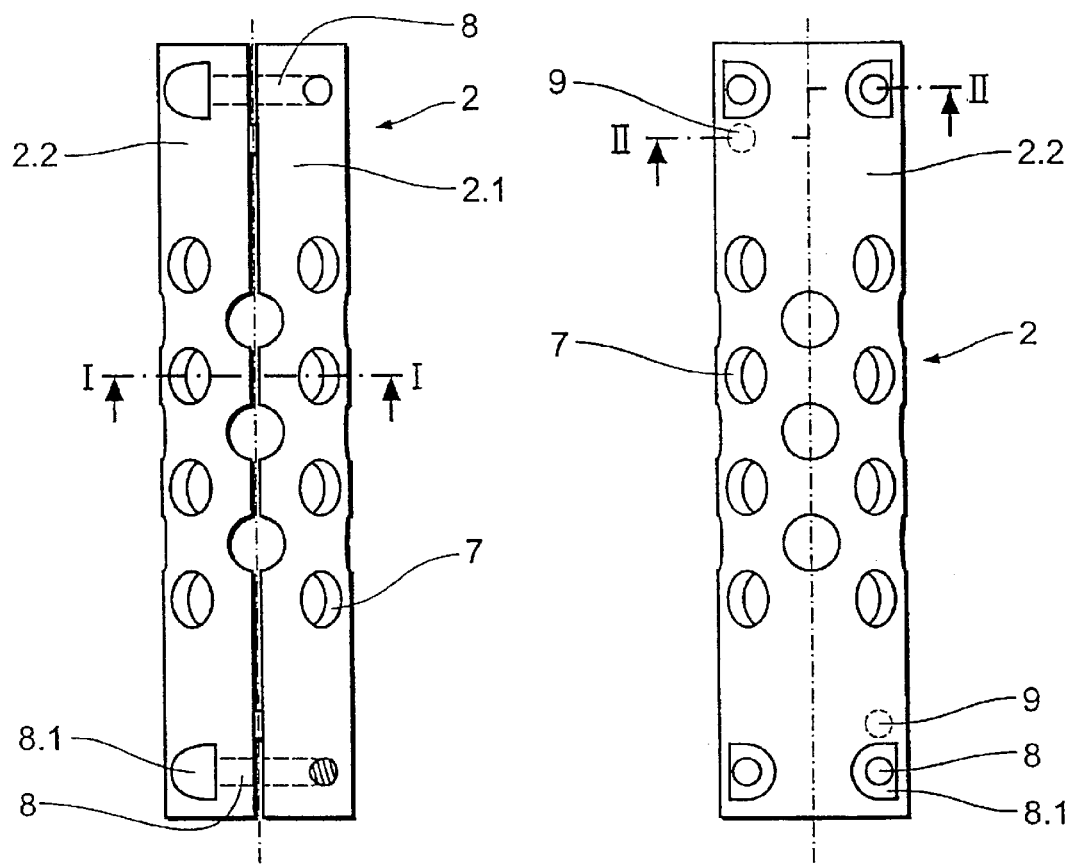
Fig. 2a  Fig. 2c
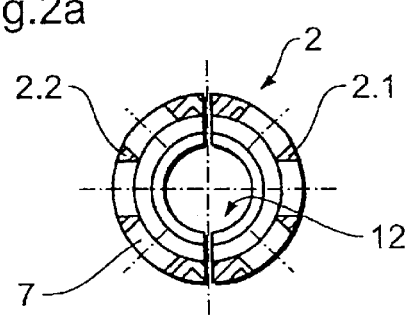
Fig. 2b  I-I  Fig. 2d  II-II
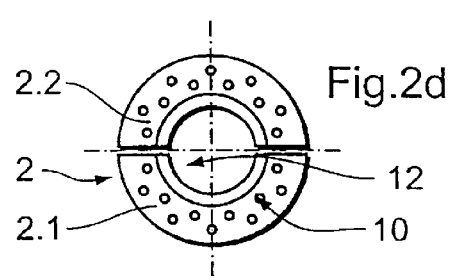
Fig. 2e

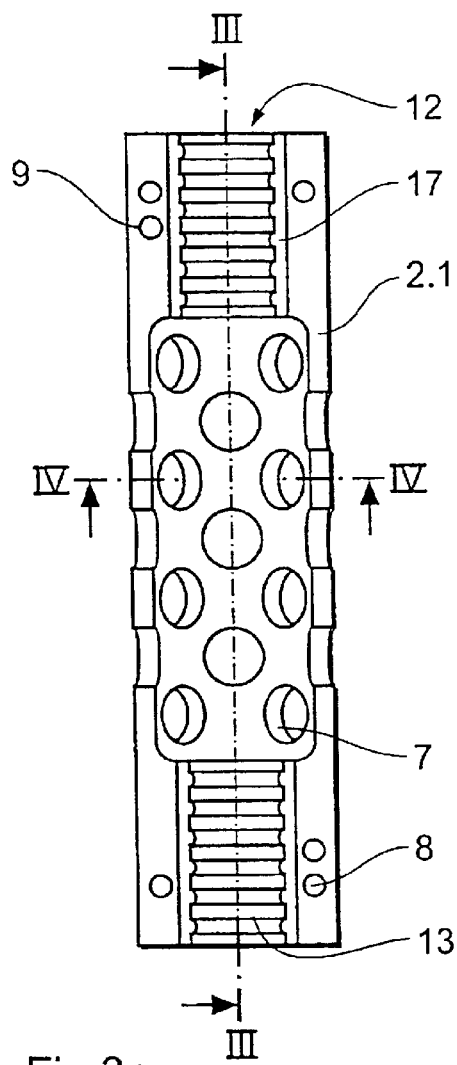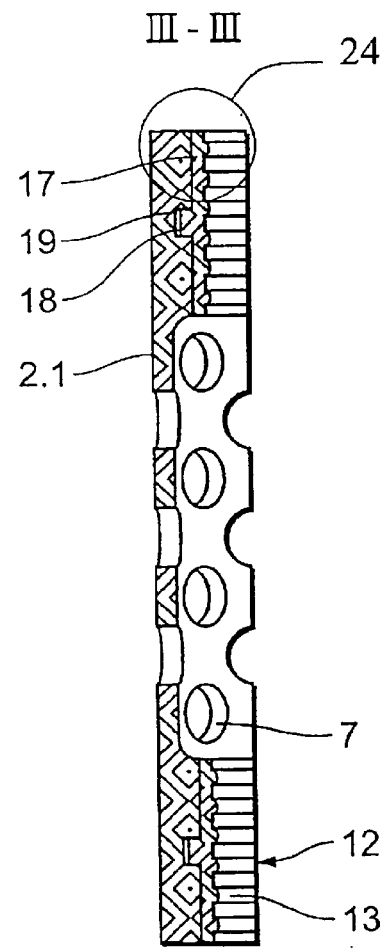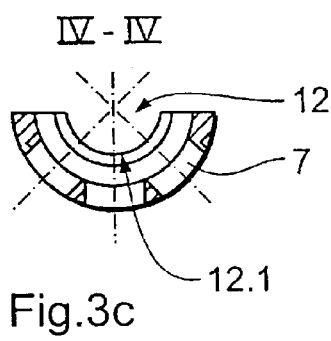
Fig.3a
Fig.3b
Fig.3c

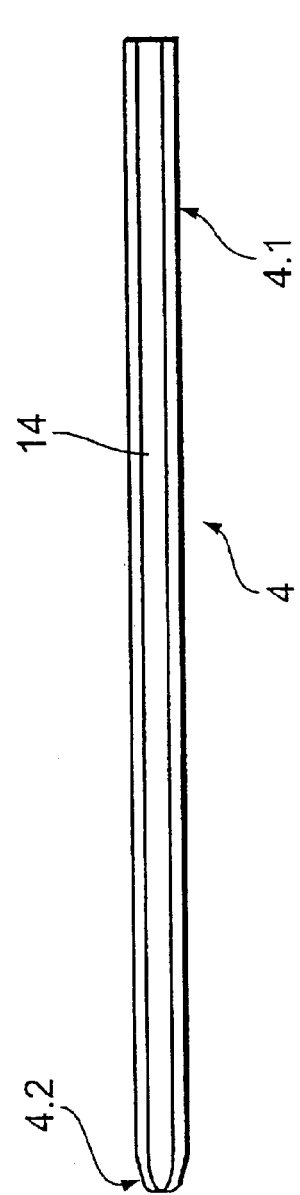
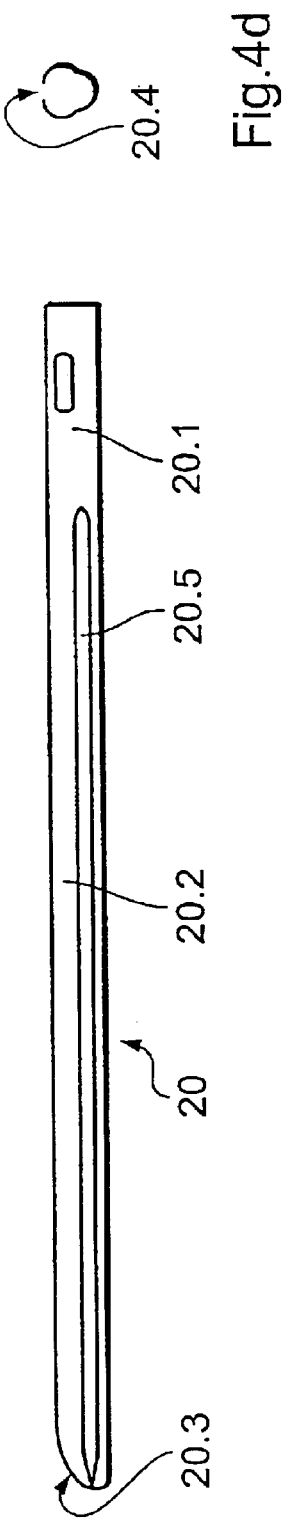

ENDOPROTHESIS

CROSS-REFERENCE TO RELATED APPLICATION

This application is a continuation of U.S. Ser. No. 09/242,410 filed Feb. 16, 1999 now U.S. Pat. No. 6,454,810, and claims the priority of German patent application Serial No. 196 33 865.4 filed Aug. 16, 1996 and PCT/DE97/01819 filed Aug. 18, 1997, the disclosure of each of the foregoing documents, as well as that of each U.S. and foreign patent and patent application mentioned in the specification of the present application, being incorporated herein by reference.

BACKGROUND OF THE INVENTION

The invention relates to an endoprosthesis.

With extensive osseous defects, for example an ostectomy caused by a tumor, it is possible to retain most of the function of the respective limbs and to avoid an otherwise necessary amputation by using an endoprosthesis that balances out the existing bone loss.

The German Unexamined Published Patent No. DE 35 28 728 discloses an endoprosthesis for replacing the center section of an elongated bone with a sleeve-shaped spacing element, having a stationary pin on one end and a pin that is arranged axially displaceable inside the spacing element on the other end.

The above-described endoprosthesis has the disadvantage of requiring a relatively large distance between the bone fragments to be joined, despite its two-piece construction. Such a large extension frequently cannot be realized at all or only by causing a correspondingly extensive trauma to soft tissues, muscles or even tendons. In addition, the prosthesis provides only for a single screw-together option to secure the axially movable pin in a selected position against an undesirable axial displacement. The frictional connection necessary between the wall of the spacing element and the pin, arranged therein so as to be displaceable, to secure the desired pin position can be produced only with difficulties under the conditions of an operation.

SUMMARY OF THE INVENTION

Starting with the shortcomings in the state of the technology, it is the object of the invention in particular to specify an improved endoprosthesis. For one thing, this endoprosthesis is distinguished by a great variability in length, leads to further simplifications in operating technology and can be inserted with less trauma to the body part to be treated operatively.

The invention includes the realization that the better the adaptation of the endoprosthesis to the location of use, the lower the trauma to the body tissue during the surgical implantation of a prosthesis. Of particular advantage in this case are prostheses composed of several individual parts for which the size can be varied.

The invention furthermore includes the provision that for an endoprosthesis with pin-type securing means and a two-part, sleeve-shaped intermediate member as replacement for parts of elongated bones, the end of the rotation-symmetrical pin through a frictional connection—if necessary also a frictional and form-fitting connection—in the two-part sleeve, an axial displacement of the pin is precluded, even for higher stresses in axial direction. The frictional connection is generated by joining the two sleeve parts, preferable, by screwing them together. Prior to combining the sleeve parts, the total length of the endoprosthesis can be varied without problems through an axial displacement of the securing means protruding on one side from the intermediate member.

Specially adapted end regions of the intermediate member in the form of half shells, having a reduced diameter as compared to the remaining inside diameter, function in the manner of clamping jaws. These encircle and immobilize pin-shaped securing means in the manner of a clamp, so that the securing means can be locked into different positions. Depending on the conditions, the securing means can be secured in a more or less extended position. A rotational adjustment is also possible in the process, which is particularly important if the securing means are curved and an additional directional adjustment can be made with the rotation. Furthermore, a corresponding inside profiling of the half shells advantageously permits an adaptation to different cross sections of the securing means. The adaptation is aided by designing the half shell inside to have limited resiliency, so that an additional form adaptation can occur during the clamping operation, which results in an improved holding effect.

Special advantages can be achieved, in particular, with a local material deformation, caused by characteristic differences in the materials for the sleeve parts and the pins, which results in an increase in the surface areas that are operatively connected at the anchoring location.

In accordance with the preferred embodiment of the invention, the endoprosthesis for replacing osseous areas in the diaphysial and metaphysial region of an elongated bone comprises a two-part intermediate member that is divided in the direction of its longitudinal axis. The intermediate member has an essentially cylindrical design and can be assembled by fitting together two identically shaped half shells. Each half shell contains a semi-cylindrical recess at the end for forming a passage at both ends after the intermediate member is assembled. Pin-shaped or nail-shaped means for the intramedullary securing of the intermediate member are provided in these passages, in such a way that prior to joining the parts of the intermediate member, they can be advantageously inserted and positioned in the passage, so as to be axially displaceable. Subsequently, the securing means are anchored in the selected position inside the passages by joining the half shells, wherein the necessary frictional connection is generated preferably by screwing together the half shells. As a result, a dimensionally correct adaptation of the endoprosthesis to the patient-specific conditions is easily possible without causing excessive trauma to the area of the body that is to be treated.

In accordance with the preferred embodiment of the invention, the wall of the semi-cylindrical recess is provided with a profiling at the ends of the part elements that can be fitted together to form the intermediate member to obtain a secure anchoring of the securing means. It is advantageous to use beads for this profiling, which extend in a semi-circular shape and are arranged in rows as seen in axial direction. Another embodiment of the invention provides that inserting a semi-cylindrical sleeve part into each of the recesses of the part elements is advantageous for a possible subsequent operation. These inserted, semi-cylindrical sleeve parts are provided with a profiling of semi-circular beads, arranged in rows in axial direction and can be easily replaced in case of wear. To secure the sleeve part against an axial displacement, for example, the recess contains an annular groove. A ring-shaped bead, arranged at the periphery of the sleeve part, engages in this groove.

One advantageous modification of the invention provides that the annular beads of the profiling on the inside walls of the passages, formed when the half-shells of the intermediate member of the endoprosthesis are joined, as well as of the beads for the semi-cylindrical sleeve parts have a trapeze-shaped or triangular, respectively an essentially semi-circular cross-sectional profile. A deformation of either the securing means shank which is positioned inside a passage, or a deformation of the annular beads on the passage wall is favorably ensured in this way, depending on the strength ratio of the materials used for the securing means and the shell-shaped part elements of the intermediate member of the endoprosthesis. Such a deformation results in each case in an enlargement of the surface areas for the operational engagement of the individual parts of the endoprosthesis according to the invention and thus to an increase in the desired frictional connection for anchoring the securing means.

According to another modification of the invention, it is favorable if the semi-circular beads of the recesses forming the passages or of the semi-cylindrical sleeve parts are divided into individual segments in tangential direction to ensure a good frictional and form-fitting connection between intermediate member and securing means.

Based on another embodiment of the invention, the shank for the intradmedullary securing means has a profiling, which corresponds essentially to the profiling provided in the passages of the intermediate member of the endoprosthesis. This design of the securing means permits a combination frictional and form-fitting connection when the part elements of the intermediate member with inserted securing means are joined. The endoprosthesis is adapted gradually to the size of the bone defect to be surgically corrected in each case, wherein the possibilities for an exact adaptation are determined by the respective size dimensions of the profiling.

Independent of the configuration of the shank for the securing means, which must be anchored in the intermediate member, grooves are provided along the shank periphery, which extend in axial direction over the total length of the securing means and are arranged in a radial-symmetrical distribution. The grooves increase the safety against turning of the securing means, which are inserted intramedullary into the bone segments to be joined.

In accordance with another advantageous embodiment of the endoprosthesis according to the invention, the securing means are designed as intramedullary nails that are preferably commercially available and have a hollow body shape. They contain a longitudinal slot, extending over a section of the nail wall or over the complete nail length. One advantageous modification of the invention provides that the end region, which can be inserted into one passage of the intermediate member, preferably consists of a solid material that allows a particularly secure anchoring in the medulla of the bone segments to be joined. On the one hand, the longitudinal slot ensures a radial elasticity. On the other hand—promoted by a growing-in of the bone material—it provides sufficient security against turning of the intramedullary anchored securing means. Depending on the situation, it may be advantageous to insert curved securing means for the purpose of adaptation to the position and/or form of the bone sections that must be joined to form a complete bone by means of the endoprosthesis according to the invention. The end regions of the securing means to be anchored inside the intermediate member do not have this essentially circular-arc shaped curvature.

To accelerate the growing-in of the endoprosthesis into the surgically treated area of implantation, a biocompatible coating is applied to the outer surface of the part elements that are joined to form the intermediate member. In addition, the surface on the end faces of the part elements contains a scarring formed by protuberances, wherein the protuberances, for example, have a hemispherical shape. The walls of the part elements are provided with essentially circular openings.

In accordance with another modification of the invention, the sides of the part elements that face each other in the assembled state of the intermediate member are provided with latching means in the form of pegs and holes, which make it possible to secure the position of the part elements prior to the joining.

The individual parts for the endoprosthesis fitted together according to the invention are fashioned from a body-compatible and body-resistant, preferably metallic material such as titanium, tantalum, niobium or corresponding alloys.

BRIEF DESCRIPTION OF THE DRAWINGS

Other advantageous aspects of the invention are shown in further detail in the following with the aid of the Figures and together with the description of the preferred embodiment of the invention.

FIG. 2a Shows the intermediate member for the endoprosthesis, shown in FIG. 1, in a view from above;

FIG. 2b Shows the representation of a section along line I—I according to the FIG. 2a;

FIG. 2c Shows an intermediate member according to FIG. 2a, turned by 90°;

FIG. 2d Shows the representation of a section along line II—II, according to FIG. 2c;

FIG. 2e Shows the intermediate member of the endoprosthesis, shown in FIGS. 2a and 2c, in a view from the front;

FIG. 3a Shows a part element of the intermediate member, shown in FIGS. 2a and 2c, in a view from above;

FIG. 3b Shows a view of a section along the line III—III in FIG. 3a;

FIG. 3c Shows a view of a section along the line IV—IV in FIG. 3a;

FIG. 4a Shows the preferred embodiment of a securing means for the endoprosthesis according to the invention;

FIG. 4b Shows the securing means shown in FIG. 4a, in a view from the left;

FIG. 4c Shows another advantageous embodiment of a securing means;

FIG. 4d Shows the securing means shown in FIG. 4c, in a view from the left;

FIG. 5a Shows a favorable modification of the securing means shown in FIG. 4a;

FIG. 5b Shows a representation of the view of a longitudinal section through the securing means according to FIG. 5a;

FIG. 5c Shows a representation of a section along the line V—V according to FIG. 5a;

Figure 1:
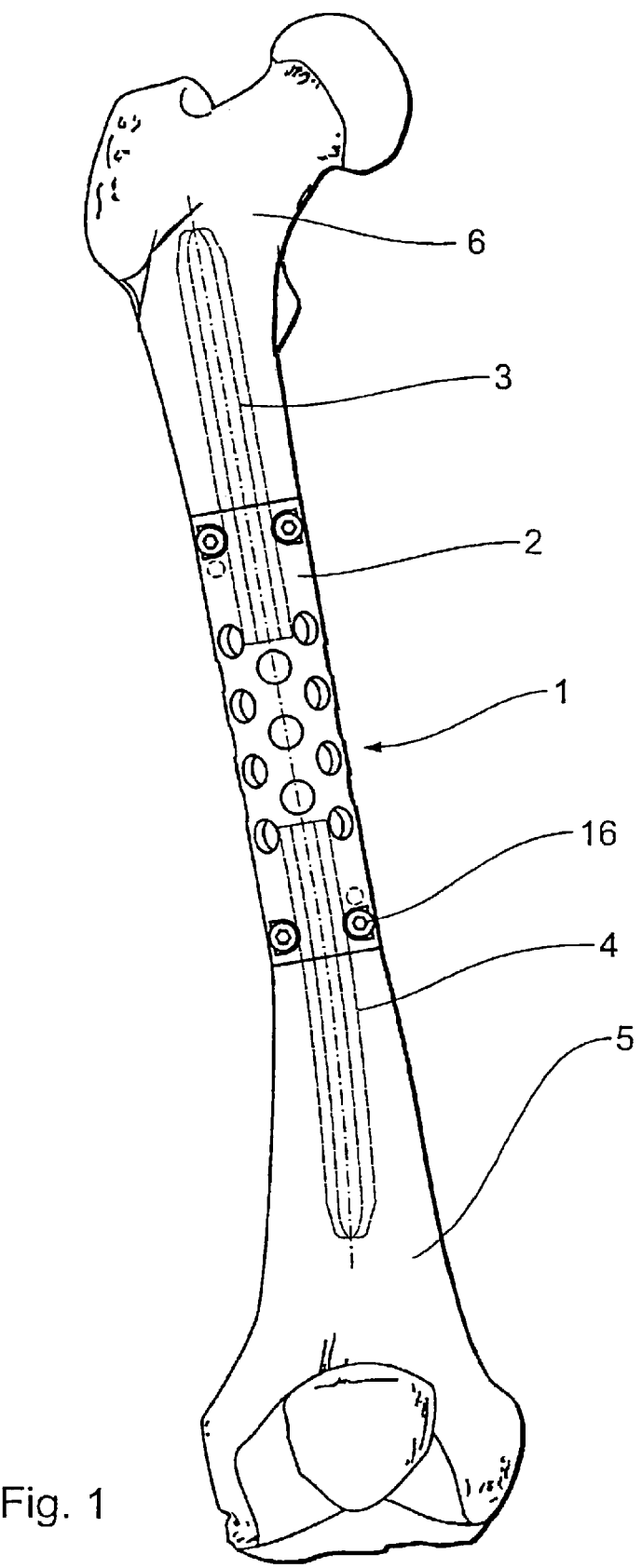
FIG. 1 Shows the preferred embodiment of the endoprosthesis according to the invention, in the implanted state.

The center section of the femur, shown in the perspective drawing in FIG. 1, is replaced with an endoprosthesis 1. The endoprosthesis 1 comprises an intermediate member 2 that equalizes a bone defect, incurred as a result of an accident or illness, and joins the two bone segments 5 and 6. The bone segments 5 and 6 and the intermediate member 2 are joined with the securing means 3 and 4 which are inserted into the medullary space of the bone segments 5 and 6 and are then connected form-fittingly and frictionally with the two-part intermediate member 2. The curvature of the securing means 3, 4 varies, so that these can be adapted optimally to the (not drawn in) medullary space of the bone segments 5 and 6. The individual parts of the intermediate member 2 are joined by screwing them together (compare the positions 2.1 and 2.2 according to FIGS. 2a to 2e and 3a to 3c). In that case, the shanks of securing means 3, 4 occupy about one third of the internal hollow space of intermediate member 2 on each side. The self-locking screw means used in this case are given the reference number 16 and are turned with the aid of a wrench for socket head cap screws.

The intermediate member 2 of the endoprosthesis is shown in FIGS. 2a to 2e as view from above, that is as view of the sections along lines I—I and II—II and as view from the front. The FIGS. 3a to 3c show a part element 2.1 of the intermediate member 2 in a view from above and a view of the sections along the lines III—III and IV—IV.

The part elements 2.1 and 2.2 of the intermediate member 2 are formed as half shells, having at least essentially the same design. With preferred embodiments, these half shells can also be identical in form in that they have a symmetrical design, rotated by 180°, and complement each other to form a complete hollow cylinder. In that case, the raised sections on one part, arranged so as to be displaced by 180°, engage in the corresponding recesses on the other part, thus forming guides.

The half shells 2.1 and 2.2 respectively have a narrowed, semi-cylindrical recess 12.1 at their ends, which together form a circular, cylindrical passage 12 when the intermediate member 2 is assembled. The semi-cylindrical sleeve parts 17 provided to fit inside this passage can be replaced when they are worn out. In order to secure the axial position of the sleeve parts 17, they are provided with a circular bead 18 with rectangular cross section on the outside wall. This bead engages in a corresponding groove 19 in the recess 12.1 of part element 2.1.

To simplify the position-correct assembly of the intermediate member 2 under the conditions of an operation, the part elements 2.1 and 2.2 are provided with locking means, respectively configured as bore 9 and pin 9.1, which must be engaged so that the screw means (compare position 16 in FIG. 1) inserted into the bores 8 can securely grip the thread 8.2, and the passage 12 has a circular cross section. Once the intermediate member 2 is assembled, the screw means are supported in the recess 8.1.

The walls of the part elements 2.1 and 2.2 contain a plurality of circular, evenly distributed openings 7 which, in connection with a (not shown) biocompatible surface coating, support the growing-in of connective tissue and thus ensure a good anchoring of the implanted endoprosthesis. The end faces of the part elements 2.1, 2.2, which are operatively connected to the bone segments 5, 6 following the implantation, have a structured surface with semi-circular protuberances 10 to facilitate anchoring in the bone mass that forms after implantation.

The sleeve parts 17, which are inserted into the recesses 12.1, have a profiling 13 in the shape of semi-circular beads on the inside wall. This profiling ensures good contact with the securing means, inserted axis-parallel therein (compare the positions 3 and 4 in FIG. 1). Owing to the surface pressure generated after the part elements 2.1 and 2.2 are screwed together, their ends are frictionally anchored inside the passages 12, so that an axial displacement due to normal mechanical stress on the endoprosthesis can be ruled out.

Figure 3D:
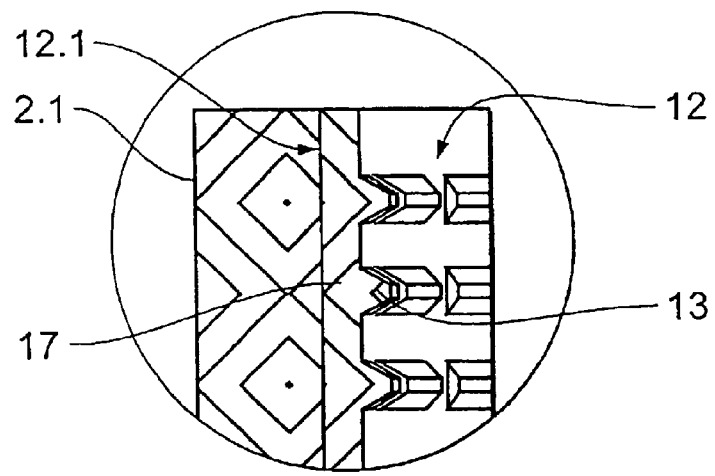
FIG. 3d Shows a representation of the detail 24 according to FIG. 3b.
Figure 3E:
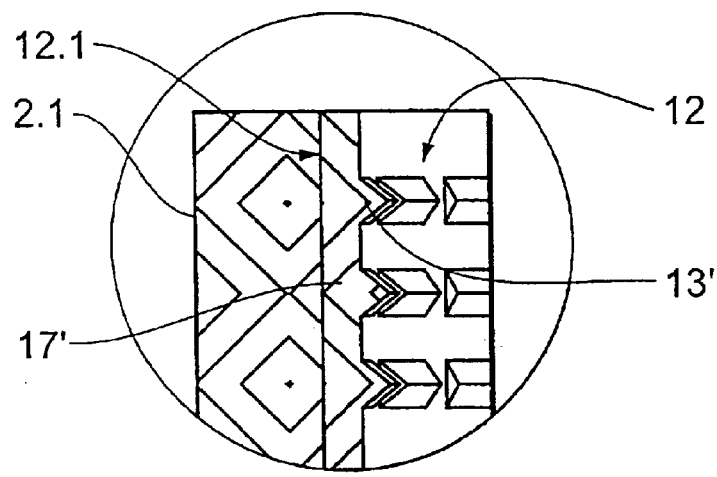
FIGS. 3e/3f Shows advantageous modifications of the invention illustrated in FIG. 3d.
Figure 3F:
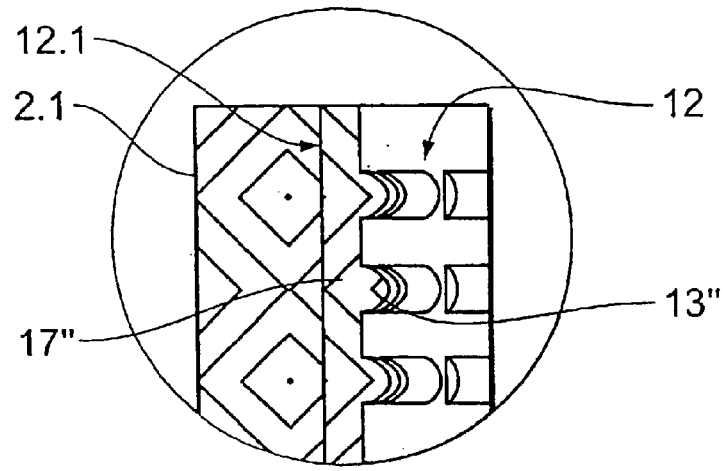

Advantageous cross-sectional profiles 13, 13' and 13" of differently designed beads for the semi-cylindrical sleeve parts 17, 17', 17" are shown in FIGS. 3d, 3e and 3f as detail 24. In dependence on the mechanical strength of the materials used for the fixation means or the part elements of the intermediate member, either the beads or the surface area of the securing means, inserted into the passage 12, are deformed when the part elements of the intermediate member are screwed together, in such a way that an enlarged area of operative engagement is created which then functions to generate the necessary friction for a safe anchoring of the securing means. Trapezoidal (FIG. 3d), triangular (FIG. 3e) or semi-circular cross-sectional profiles (FIG. 3d) of the beads are advantageous for such a deformation behavior. The semi-circular beads are divided into individual segments in tangential direction, so as to achieve a secure frictional and form-fitting connection even for slight axial deviations, for example, between intermediate member and securing means.

In FIGS. 4a to 4d, 5a to 5c and 6a to 6c, various means for the intramedullar fixation of the intermediate member of the endoprosthesis are shown in a view from above and a view from the side or as a sectional view.

The pin-shaped securing means 4 according to FIG. 4a is made of solid material and has two longitudinal grooves 14, arranged diametrically opposite each other to prevent a turning of the means after the endoprosthesis is implanted. The end region 4.1 is anchored in the intermediate member. The pin end 4.2 is tapered, thus making it easier to insert the securing means 4 into the medulla.

The medulla nail 20 according to FIG. 4c is designed as hollow body with a taper 20.3 on one side and a slot 20.4 that extends axially over the total length.

The slot ensures a radial spring effect during the insertion into the medulla and the anchoring in the intermediate member. The longitudinal groove 20.3 functions to prevent a turning following implantation.

Figure 5A:
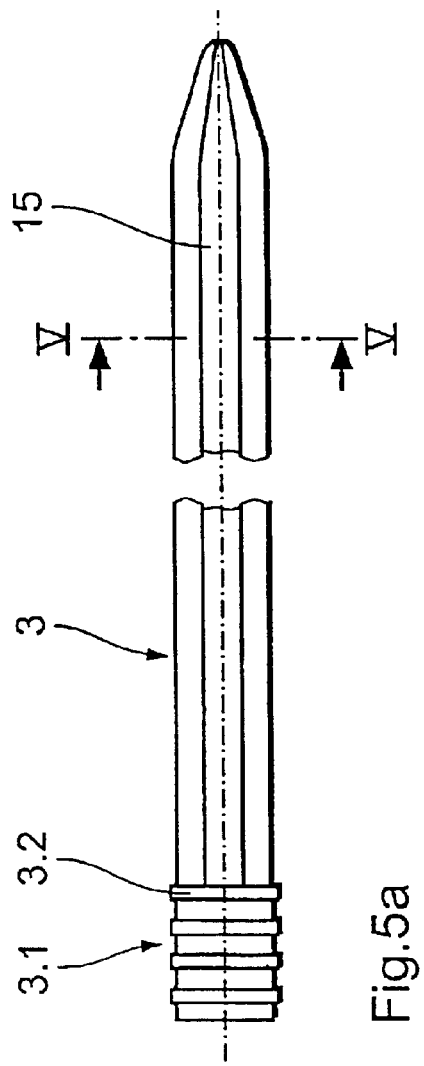
Figure 5B:
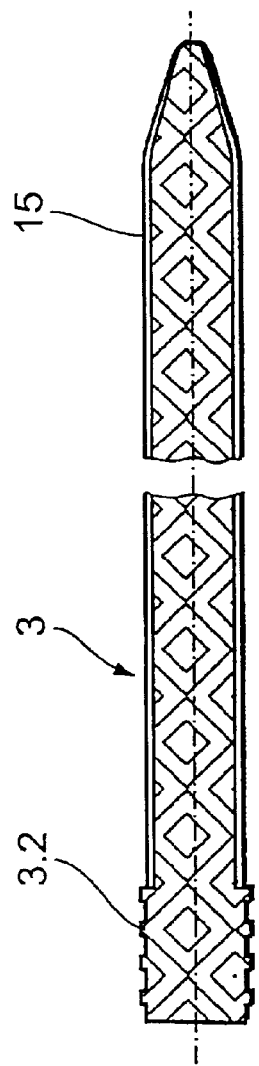
Figure 5C:
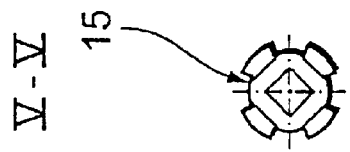

At the end 3.1 to be anchored in the intermediate member, the securing means 3, shown in FIGS. 5a to 5c, has a profiling consisting of annular beads 3.2. This profiling matches a profiling in the recesses of the part elements (e.g. compare the positions 2.1, 12.1 and 13" according to FIG. 3f) and permits a form-fitting and frictional anchoring of the profiled end of the securing means during the assembly of the intermediate member. The four longitudinal grooves 15 in a radial symmetrical arrangement are provided to secure the implanted endoprosthesis against turning.

Figures 6A, 6B:
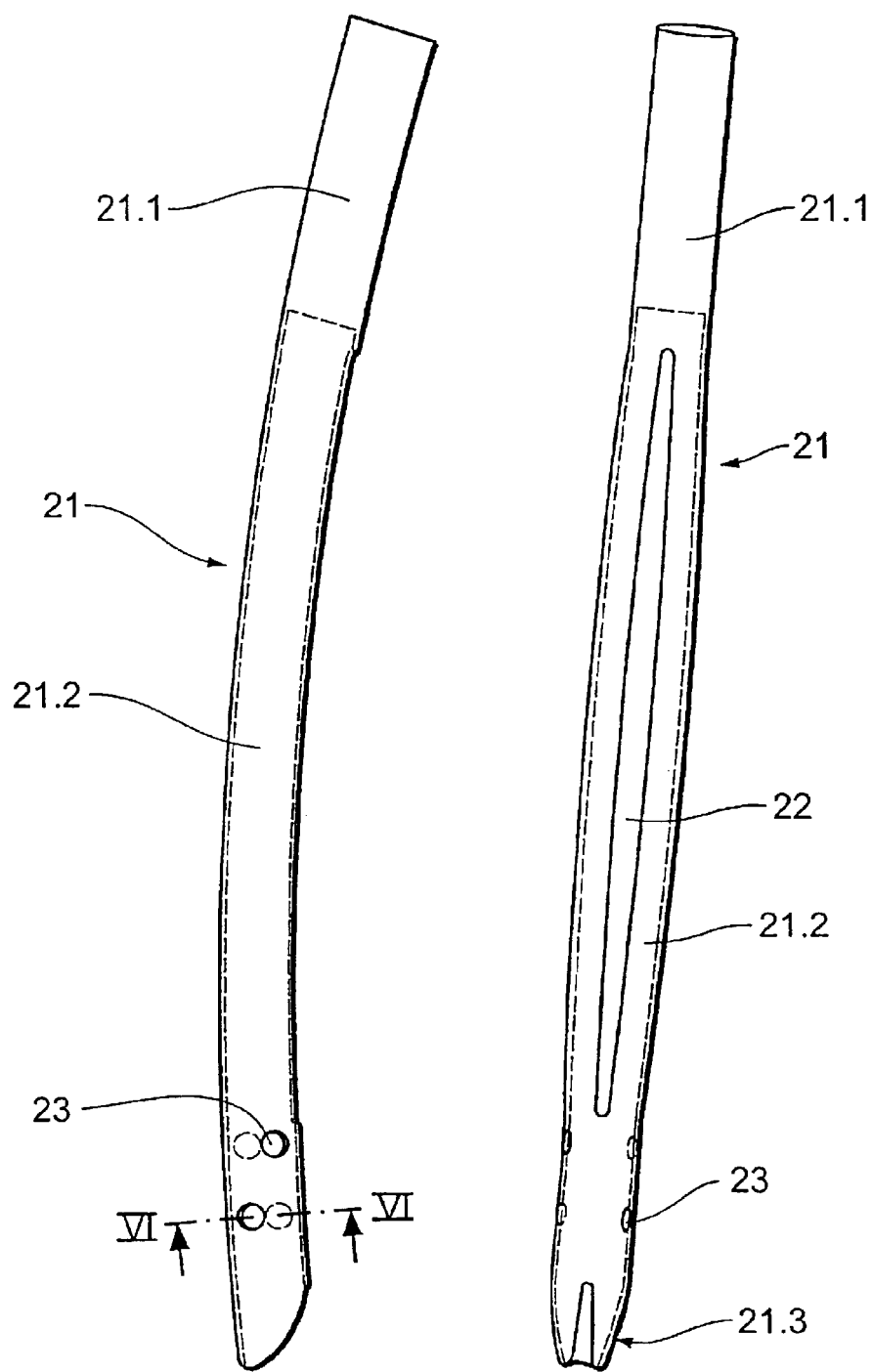
FIG. 6a Shows another embodiment of a securing means for the endoprosthesis according to the invention, in a view from above.
FIG. 6b Shows the securing means shown in FIG. 6a, after it is turned by 90°.
Figure 6C:
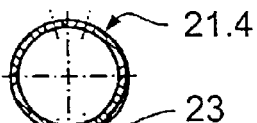
FIG. 6c Shows the representation of a section along the line VI—VI according to FIG. 6b.

The intramedullary nail 21, shown in FIGS. 6a to 6c, is designed as hollow body, for which the end 21.2 for anchoring in the intermediate member is made of solid material. The elasticity of the hollow shank 21.2 is supported by two longitudinal grooves 22. The tapering shank tip 21.3 and the openings 23, located therein, make it easier to insert the securing means into the intramedullary canal. The slight curvature of the intramedullary nail shank facilitates the adaptation of the endoprosthesis to curved segments of the medullary space of bone sections to be joined.

The design of the invention is not limited to the aforementioned, preferred exemplary embodiments. Rather, a number of variants are conceivable, which make use of the solution presented, even if the embodiments are basically very different.

What is claimed is:

1. An endoprosthesis for replacing osseous areas in the diaphysial and metaphysial region of a bone and for connecting separate segments of the bone, comprising:
    at least one intramedullary securing member; and
    an intermediate member having at least one end region and being divided longitudinally into two detachably connected part elements, each at least one end region defining a respective recess so that when the two part elements are connected together each at least one end region forms an axially extending passage that retains one of the at least one intramedullary securing members, wherein said intermediate member has an outer diameter which approximately corresponds to an outer diameter of the segments of bone to be connected.

2. The endoprosthesis according to claim 1, wherein each of the at least one securing members have one of a nail shape, a pin shape, and a fracture pin shape.

3. The endoprosthesis according to claim 1, wherein each of the at least one recesses have a profiled inside wall surface.

4. The endoprosthesis according to claim 1, further comprising a biocompatible coating on the intermediate member.

5. The endoprosthesis according to claim 4, wherein the part elements of the intermediate member have faces which face the bones to be joined and a structuring is provided on the faces.

6. The endoprosthesis according to claim 5, wherein the structuring is formed by essentially hemispherical protuberances.

7. The endoprosthesis according to claim 1, wherein at least one of the at least one securing members has a curvature.

8. The endoprosthesis according to claim 7, wherein the curvature is a circular arc-shaped curvature.

9. The endoprosthesis of claim 1, wherein said intermediate member replaces the osseous areas in the diaphysial and metaphysial region of a bone.

10. The endoprosthesis of claim 1, further comprising means for detachably fixing the two part elements.

11. An endoprosthesis for replacing osseous areas in the diaphysial and metaphysial region of a bone and for connecting separate segments of the bone, comprising:
    two intramedullary securing members; and
    a connecting member having at least one end region and being divided longitudinally into two detachably connected part elements, each at least one end region defining a respective recess so that when the two part elements are connected together each at least one end region forms an axially extending passage that retains one of the intramedullary securing members, the connecting member being integrally fixed to the other intramedullary securing member.

* * * * *